US008114316B2

(12) United States Patent
Heeney et al.

(10) Patent No.: US 8,114,316 B2
(45) Date of Patent: Feb. 14, 2012

(54) MONOMERS, OLIGOMERS AND POLYMERS OF THIENO[2,3-B]THIOPHENE

(75) Inventors: Martin Heeney, Southampton (GB); Clare Bailey, Southampton (GB); Steven Tierney, Southampton (GB); Iain McCulloch, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 543 days.

(21) Appl. No.: 11/573,983

(22) PCT Filed: Jul. 23, 2005

(86) PCT No.: PCT/EP2005/008045
§ 371 (c)(1),
(2), (4) Date: Nov. 6, 2008

(87) PCT Pub. No.: WO2006/021277
PCT Pub. Date: Mar. 2, 2006

(65) Prior Publication Data
US 2009/0072200 A1  Mar. 19, 2009

(30) Foreign Application Priority Data
Aug. 21, 2004 (EP) ................................. 04019892

(51) Int. Cl.
*H01B 1/06* (2006.01)
*H01B 1/24* (2006.01)
(52) U.S. Cl. ..................... 252/510; 252/299.2; 252/500; 514/443; 546/80; 549/50
(58) Field of Classification Search .................. 252/500, 252/299.2, 510; 514/443; 549/50; 546/80
See application file for complete search history.

(56) References Cited

U.S. PATENT DOCUMENTS

| 4,639,328 | A | | 1/1987 | Krause et al. | |
|---|---|---|---|---|---|
| 4,806,562 | A | * | 2/1989 | Hartman et al. | ............... 514/443 |
| 4,929,549 | A | | 5/1990 | Hartman et al. | |
| 7,183,418 | B2 | * | 2/2007 | Heeney et al. | .................. 549/50 |
| 2003/0021912 | A1 | | 1/2003 | Farrand et al. | |
| 2005/0090640 | A1 | | 4/2005 | Heeney et al. | |
| 2009/0072200 | A1 | * | 3/2009 | Heeney et al. | ................. 252/500 |

FOREIGN PATENT DOCUMENTS

| AU | 6135294 A | 8/1994 |
|---|---|---|
| AU | 7564296 A | 6/1997 |
| AU | 773218 B2 | 5/2004 |
| DE | 4422488 A1 | 1/1996 |
| EP | 0144013 A | 6/1985 |
| EP | 0382537 A | 8/1990 |
| EP | 1275651 A | 1/2003 |
| EP | 1510535 A | 3/2005 |
| JP | 2005 043507 A | 2/2005 |
| WO | WO 9418192 A | 8/1994 |
| WO | WO 9719039 A | 5/1997 |
| WO | WO 0127103 A | 4/2001 |

OTHER PUBLICATIONS

Comel et al., "Efficient ONe Pot Preparation of Variously Substituted Thieno[2,3-b]thiophene", J. Heterocyclic Chem., 38, 1167-1171, (2001).*
Lazzaroni R et al: "Electronic Structure of Conducting Polymers From Heteroaromatic Bicyclic Compounds" Synth Met Sep. 1986, vol. 21, No. 2, Aug. 18, 1986, pp. 189-195, XP002352795.*
Database CA 'Online1 Chemical Abstracts Service, Columbus, Ohio, US; Bruce, Joseph et al: "Substitution and polymerization reactions of thiopene and the isomeric thiopthenes" XP002352806 retrieved from STN Database accession No. 1948: 23251 abstract & Journal of the Institute of Petroleum, 34, 226-35 CODEN: JIPEA6; ISSN: 0020-3068, 1948.*
Database Caplus 'Online! Chemical Abstracts Service, Columbus, Ohio, US; Kojima, Takashi et al: "Holographic memory media and compositions therefore with high diffraction efficiency and sensitivity" XP002352805 retrieved from STN Database accession No. 2005: 135824 compounds with RN 152487-69-9, 844471-42-7, 8444143-8, 844471-44-9 and respective polymers abstract.
Lazzaroni R et al: "Electronic Structure of Conducting Polymers From Heteroaromatic Bicyclic Compounds" Synth Met Sep. 1986, vol. 21, No. 2, Aug. 18, 1986, pp. 189-195, XP002352795 tables 1, 3.
Database Ca Online1 Chemical Abstracts Service, Columbus, Ohio, US; Bruce, Joseph et al: "Substitution and polymerization reactions of thiopene and the isomeric thiopthenes" XP002352806 retrieved from STN Database accession No. 1948: 23251 abstract & Journal of the Institute of Petroleum, 34, 226-35 CODEN: JIPEA6; ISSN: 0020-3068, 1948.
Abdallah, S. et al., "Synthesis and antiplatelet activity of 1-tert-Butylamino-3-(3-thienyloxy)-2-propanols," Arch. Pharm. Pharm. Med. Chem., 1996, vol. 329, pp. 216-222.
Bao, Z. et al., "Soluble and processable regioregular poly(3-hexylthiophene) for thin film field-effect transistor applications with high mobility," Appl. Phys. Lett., Dec. 23, 1996, vol. 69, No. 26, pp. 4108-4110.
Bruce, J. et al., "Substitution and polymerization reactions of thiophene and the isomeric thiopthenes," Journal of the Institute of Petroleum, 1948, vol. 34, pp. 226-35, XP-002352806. English Abstract of Kossmehl, G. et al., "Synthesen und Charakterisierung von poly(thieno[2,3,-b]thiophen-2,5-diylvinylenarylenvinylen) en, Poly(thieno[3,2-b]thiphen-2,5-diyvinylenarylenvinylen)en und einigen Modellverbindungen," Makromol. Chem. 1982, vol. 183, pp. 2747-2769.
Fuller, L. S. et al., "Synthesis of polyfuntionalized thiophenes and enediynes via ring-opening reactions of 3-lithiated thieno[2,3-b] (and [3,2-b])thiophenes, 3,4-dilithiated thieno[2,3-b]thiophenes and 3,6-dilithiated thieno [3,2-b]thiophenes," Chem. Commun., 1997, pp. 2355-2356.

(Continued)

*Primary Examiner* — Khanh Tuan Nguyen
(74) *Attorney, Agent, or Firm* — Millen, White, Zelano & Branigan, P.C.

(57) ABSTRACT

The invention relates to novel mono-, oligo and polymers of thieno[2,3-b]thiophene, to their use as semiconductors or charge transport materials, in optical, electro-optical or electronic devices like LCDs, optical films, FETs or OFETs for TFT-LCDs and IC devices such as RFID tags, electroluminescent devices in flat panel displays or photovoltaic or sensor devices, and further relates to a FET, light emitting device or ID tag comprising the novel polymers.

18 Claims, No Drawings

OTHER PUBLICATIONS

Hayashi, N. et al., "Clathrate formations with isomeric host compounds based on thieno[3,2-b]thiophene and thieno[2,3-b]thiohene: Inclusion Modes and crystal stuctures," J. Org. Chem., 1995, vol. 60, pp. 6342-6347.

Kossmehl, G. et al., "Synthesen und Charakterisierung von poly(thieno[2,3,-b]thiophen-2,5-diylvinylenarylenvinylen)en, Poly(thieno[3,2-b]thiphen-2,5-diyvinylenarylenvinylen)en und einigen Modellverbindungen," Makromol. Chem. 1982, vol. 183, pp. 2747-2769.

Lazzaroni, R. et al., "Electronic structure of conducting polymers from heteroaromatic bicyclic compounds," Synthesis Metals, 1987, vol. 21, pp. 189-195.

Meunier, P. et al., "Heterocyclic series. XXIII. Synthesis of iodothieno[2,3-," Bulletin de la Societe Chimique de France, 1974, XP-002352807.

Mitsubishi Chemical Corp., "Holographic memory media and compositions therefore with high diffraction efficiency and sensitivity," Publication Date: Feb. 17, 2005, English Abstract of JP-2005 043507.

Otsubo, T. et al., "Synthesis, structures, and properties of 2,3,6,7-Tetrathiabenzo[1,3-*cd*:4,6-*c1d1*] dipentalene and Its Methyl, Ethyl, Methylthio, and Ethylthio derivatives: novel fused polynuclear heteroarenes," Bull. Chem. Soc. Jpn., 1993, vol. 66, pp. 2033-2041.

Sirringhaus, H. et al., "Integrated optoelectronic device based on conjugated polymers," Science, Jun. 12, 1998, vol. 280, pp. 1741-1744.

Zhang, X. et al., "Alkyl-substituted thieno[3,2-b]thiophene polymers and their dimeric subunits," Macromolecules, 2004.

* cited by examiner

MONOMERS, OLIGOMERS AND POLYMERS OF THIENO[2,3-B]THIOPHENE

FIELD OF INVENTION

The invention relates to novel mono-, oligo- and polymers of thieno[2,3-b]thiophene. The invention further relates to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices. The invention further relates to a field effect transistor, light emitting device or ID tag comprising the novel polymers.

BACKGROUND AND PRIOR ART

Organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semi-conducting material and the current on/off ratio, so the ideal semiconductor should have a low conductivity in the off state, combined with a high charge carrier mobility ($>1\times 10^{-3}$ cm$^2$V$^{-1}$ s$^{-1}$). In addition, it is important that the semi-conducting material is relatively stable to oxidation i.e. it has a high ionisation potential, as oxidation leads to reduced device performance.

Regioregular head-to-tail poly(3-hexylthiophene) has been reported with charge carrier mobility between $1\times 10^{-5}$ and $4.5\times 10^{-2}$ cm$^2$ V$^{-1}$ s$^{-1}$, but with a rather low current on/off ratio between 10 and $10^3$ [see Z. Bao et al., *Appl. Pys. Lett.*, 1996, 69, 4108]. This low on/off current is due in part to the low ionisation potential of the polymer, which can lead to oxygen doping of the polymer under ambient conditions, and a subsequent high off current [see H. Sirringhaus et al., *Adv. Solid State Phys.*, 1999, 39, 101].

A high regioregularity leads to improved packing and optimised microstructure, leading to improved charge carrier mobility [see H. Sirringhaus et al., *Science*, 1998, 280, 1741-1744; H. Sirringhaus et al., *Nature*, 1999, 401, 685-688; and H. Sirringhaus, et al., *Synthetic Metals*, 2000,111-112, 129-132]. In general, poly(3-alkylthiophenes) show improved solubility and are able to be solution processed to fabricate large area films. However, poly(3-alkylthiophenes) have relatively low ionisation potentials and are susceptible to doping in air.

It is an aim of the present invention to provide new materials for use as semiconductors or charge transport materials, which are easy to synthesize, have high charge mobility, good processibility and oxidative stability.

Another aim of the invention is to provide new semiconductor and charge transport components, and new and improved electrooptical, electronic and electroluminescent devices comprising these components, like field effect transistors (FET) as components of integrated circuitry or of thin film transistors (TFT), and organic light emitting diode (OLED) applications like electroluminescent displays or backlights of liquid crystal displays.

Other aims of the invention are immediately evident to those skilled in the art from the following description.

The inventors have found that these aims can be achieved by providing mono-, oligo- and polymers of thieno[2,3-b] thiophene as claimed in the present invention.

G. Koβmehl et al., Makromol. Chem. 1982, 183, 2747-2769 discloses poly(thieno[2,3-b]thiophene-2,5-divinylene-arylenes) and methods of their preparation from corresponding aldehyde monomers, but does not disclose compounds according to the present invention.

SUMMARY OF THE INVENTION

The invention relates to monomeric, oligomeric and polymeric compounds of formula I

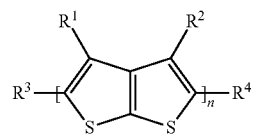

wherein $R^1$ and $R^2$ are independently of each other H, halogen, optionally substituted aryl or heteroaryl, P-Sp-, P*-Sp-, or straight chain, branched or cyclic alkyl with 1 to 20 C-atoms, which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —O—CO—O—, —S—CO—, —CO—S—, —CX$^1$═CX$^2$— or —C≡C— in such a manner that O and/or S atoms are not linked directly to one another, $R^3$ and $R^4$ independently of each other have one of the meanings of $R^1$ or denote —Sn(R$^0$)$_3$, —B(OR')(OR"), —CH$_2$Cl, —CHO, —CH═CH$_2$ or —SiR$^0$R$^{00}$R$^{000}$, R$^0$, R$^{00}$, R$^{000}$ are independently of each other H, aryl or alkyl with 1 to 12 C-atoms, R' and R" are independently of each other H or alkyl with 1 to 12 C-atoms, or OR' and OR" together with the boron atom form a cyclic group having 2 to 20 C atoms, $X^1$ and $X^2$ are independently of each other H, F, Cl or CN, P is a polymerisable group, P* is a group that can be converted to or substituted by a polymerisable group P, Sp is a spacer group or a single bond, n is an integer $\geq 1$, wherein the recurring units can be identical or different and, in case n is 1 and $R^1$ and $R^2$ are H, then one or both of $R^3$ and $R^4$ are P-Sp-, halogen, —Sn(R$^0$)$_3$, —B(OR')(OR"), —CH$_2$Cl, —CH═CH$_2$, —SiR$^0$R$^{00}$R$^{000}$.

The invention further relates to a semiconducting, electroluminescent or charge transport material, component or device comprising at least one compound as defined above and below.

The invention further relates to the use of the compounds according to the present invention as semiconductors or charge transport materials, in particular in optical, electrooptical or electronic devices, like for example in field effect transistors (FET) as components of integrated circuitry, as thin film transistors in flat panel display applications like liquid crystal displays (LCD), for Radio Frequency Identification (RFID) tags, or in semiconducting components for displays or organic light emitting diodes (OLED), including both the charge transport and electroluminescent layers.

The invention further relates to the use of the compounds according to the present invention as electroluminescent materials, for OLED applications such as electroluminescent displays or backlights of displays, in photovoltaic or sensor devices, as electrode materials in batteries, as photoconductors, for electrophotographic applications like electrophotographic recording, for organic memory devices, for detecting and discriminating DNA sequences, and as alignment layer in LCD or OLED devices.

The invention further relates to an optical, electrooptical or electronic device, FET, integrated circuit (IC), TFT, OLED or alignment layer comprising a semiconducting or charge transport material, component or device according to the invention.

The invention further relates to a TFT or TFT array for flat panel displays, radio frequency identification (RFID) tag, electroluminescent display or backlight comprising a semiconducting or charge transport material, component or device or a FET, IC, TFT or OLED according to the invention.

The invention further relates to a security marking or device comprising a FET or an RFID tag according to the invention.

DETAILED DESCRIPTION OF THE INVENTION

Formula I covers mono-, oligo- and polymers of thieno[2,3-b]thiophene. The polymers can be homopolymers, i.e. having identical recurring units, or copolymers having different recurring units of formula I. Particularly preferred are homopolymers of formula I having identical recurring units.

Especially preferred is regioregular 3-substituted poly(thieno[2,3-b]thiophene), in particular regioregular 3-alkyl substituted poly(thieno[2,3-b]thiophene) of formula I. This material can be thought of as an analogue of poly(3-alkylthiophene), which shows very high charge carrier mobility when the regioregularity is high (>96%) and is thus suitable for use in semiconductor devices like transistors. Highly regioregular polymers can self-organise into well ordered lamellar sheets, which results in high charge carrier mobility.

However, a drawback of PAT is that it has only limited air stability, resulting in high off-currents and a loss of transistor behaviour when the device is operated in air without an appropriate oxygen barrier. The doping of the material by oxygen is related to the low ionisation potential of the conjugated polymer.

In contrast, polymers of the present invention retain the desirable high charge carrier mobility because of their ability to also self-organise into well packed structures, but crucially improve the air stability of the material by lowering the ionisation potential and preventing doping by oxygen. The polymers show improved air stability because the thieno[2,3]thiophene unit is not able to form delocalised quinodal type resonance structures with adjacent aromatic units. This limits the effective conjugation length of the polymers, thus lowering the HOMO level and increasing ionisation potential.

The compounds according to the invention are thus especially useful as charge transport semiconductors. Introduction of alkyl side chains into the thienothiophene group further improves solubility and solution processability of the polymers.

Especially preferred are compounds of formula I wherein
n is an integer from 2 to 5000, preferably from 10 to 5000, very preferably from 100 to 1000,
the molecular weight (Mw) is from 5000 to 300,000, in particular from 20,000 to 100,000,
n is 1,
$R^1$ or $R^2$ is H,
$R^1$ and $R^2$ are different from H,
$R^1$ and $R^2$ are identical,
one of $R^1$ and $R^2$ is H and the other is selected from $C_1$-$C_{20}$-alkyl, $C_1$-$C_{20}$-alkoxy, $C_1$-$C_{20}$-alkenyl, $C_1$-$C_{20}$-alkynyl, $C_1$-$C_{20}$-thioalkyl, $C_1$-$C_{20}$-silyl, $C_1$-$C_{20}$-ester, $C_1$-$C_{20}$-amino, $C_1$-$C_{20}$-fluoroalkyl, and optionally substituted aryl or heteroaryl, very preferably $C_1$-$C_{20}$-alkyl or $C_1$-$C_{20}$-fluoroalkyl,
$R^1$ and $R^2$ are selected from $C_1$-$C_{20}$-alkyl, $C_1$-$C_{20}$-alkoxy, $C_1$-$C_{20}$-alkenyl, $C_1$-$C_{20}$-alkynyl, $C_1$-$C_{20}$-thioalkyl, $C_1$-$C_{20}$-silyl, $C_1$-$C_{20}$-ester, $C_1$-$C_{20}$-amino, $C_1$-$C_{20}$-fluoroalkyl, and optionally substituted aryl or heteroaryl, very preferably $C_1$-$C_{20}$-alkyl or $C_1$-$C_{20}$-fluoroalkyl,
one or both of $R^1$ and $R^2$ are selected from alkyl or fluoroalkyl with 4 to 20, preferably 6 to 15 C-atoms,
P* is —OH or —O—Si—$R^0 R^{00} R^{000}$, preferably wherein $R^0$, $R^{00}$ and $R^{000}$ are identical or different groups selected from aryl or $C_{1-12}$-alkyl, preferably $C_1$-$C_6$-alkyl, like methyl, ethyl, isopropyl, tert-butyl or phenyl,
$R^3$ and $R^4$ are selected from H, halogen, $Sn(R^0)_3$, $B(OR')(OR'')$, $CH_2Cl$, $CHO$, $CH=CH_2$, $SiR^0 R^{00} R^{000}$ and optionally substituted aryl or heteroaryl,
n is 1 and one or both of $R^3$ and $R^4$ are halogen which is preferably Br, Cl or 1, $Sn(R^0)_3$, $B(OR')(OR'')$, $CH_2Cl$, $CHO$, $CH=CH_2$ or $SiR^0 R^{00} R^{000}$,
at least one of $R^1$, $R^2$, $R^3$ and $R^4$ is P-Sp-,
n is 1 and one or both of $R^3$ and $R^4$ are P-Sp- or P*-Sp-.

Further preferred are regioregular polymers with a high percentage of head-to-tail (HT) couplings of formula I1

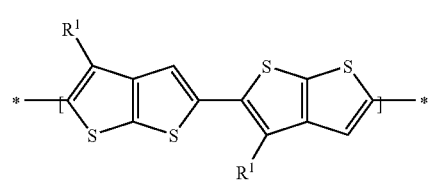

I1

The regioregularity in the polymers of the present invention is preferably at least 90%, in particular 95% or more, very preferably 98% or more, most preferably from 99 to 100%.

Regioregular polymers are advantageous as they show strong interchain pi-pi-stacking interactions and a high degree of crystallinity, making them effective charge transport materials with high carrier mobilities.

Further preferred are mono-, oligo- and polymers that are mesogenic or liquid crystalline, in particular polymers forming calamitic phases, and polymerisable monomers of formula I comprising one or more groups P-Sp- and forming calamitic phases.

Very preferred are the following polymers

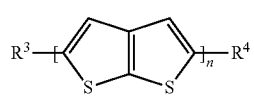

Ia

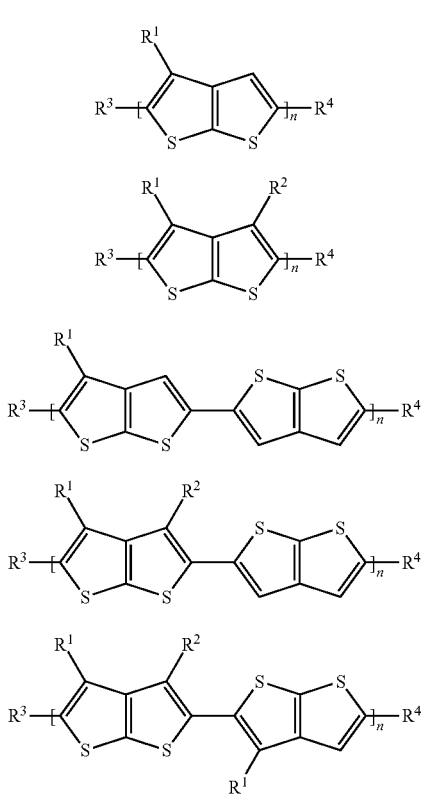

wherein $R^{1-4}$ have independently of each other one of the meanings of formula I different from H, n is as defined in formula I, and m is n/2.

If one of $R^{1-4}$ is aryl or heteroaryl, it is preferably a mono-, bi- or tricyclic aromatic or heteroaromatic group with up to 25 C atoms, wherein the rings can be fused. Heteroaromatic groups contain at least one hetero ring atom preferably selected from N, O and S. The aromatic or heteroaromatic groups are optionally substituted with one or more groups L.

L is F, Cl, Br, I, CN or straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —Si $R^0R^{00}$—, —CO—, —COO—, OCO—, —OCO—O, —S—CO—, —CO—S—, —CH=CH— or —C≡C— in such a manner that O and/or S atoms are not linked directly to one another.

Especially preferred aryl and heteroaryl groups are phenyl, fluorinated phenyl, pyridine, pyrimidine, biphenyl, naphthalene, optionally fluorinated or alkylated or fluoroalkylated benzo[1,2-b:4,5-b']dithiophene, optionally fluorinated or alkylated or fluoroalkylated thieno[3,2-b]thiophene, optionally fluorinated or alkylated or fluoroalkylated 2,2-dithiophene, thiazole and oxazole, all of which are unsubstituted, mono- or polysubstituted with L as defined above.

If one of $R^{1-4}$ is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Fluoroalkyl or fluorinated alkyl or alkoxy is preferably straight chain $(O)C_iF_{2i+1}$, wherein i is an integer from 1 to 20, in particular from 1 to 15, very preferably $(O)CF_3$, $(O)C_2F_5$, $(O)C_3F_7$, $(O)C_4F_9$, $(O)C_5F_{11}$, $(O)C_6F_{13}$, $(O)C_7F_{15}$ or $(O)C_8F_{17}$, most preferably $(O)C_6F_{13}$.

$CX^1=CX^2$ is preferably —CH=CH—, —CH=CF—, —CF=CH—, —CF=CF—, —CH=C(CN)— or —C(CN)=CH—.

Halogen is preferably F, Br or Cl.

Hetero atoms are preferably selected from N, O and S.

The polymerisable group P is a group that is capable of participating in a polymerisation reaction, like radicalic or ionic chain polymerisation, polyaddition or polycondensation, or capable of being grafted, for example by condensation or addition, to a polymer backbone in a polymeranaloguous reaction. Especially preferred are polymerisable groups for chain polymerisation reactions, like radicalic, cationic or anionic polymerisation. Very preferred are polymerisable groups comprising a C—C double or triple bond, and polymerisable groups capable of polymerisation by a ring-opening reaction, like oxetanes or epoxides.

The polymerisable group P is preferably selected from $CH_2=CW^1$—COO—,

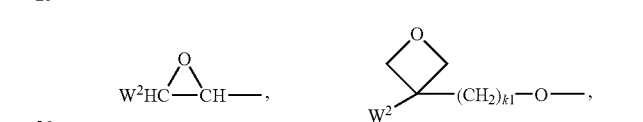

$CH_2=CW^2$—$(O)_{k1}$—, $CH_3$—CH=CH—O—, $(CH_2=CH)_2$ CH—OCO—, $(CH_2=CH)_2CH$—O—, $(CH_2=CH$—$CH_2)_2$ CH—OCO—, $(CH_2=CH$—$CH_2)_2$ N—, HO—$CW^2W^3$—, HS—$CW^2W^3$—, $HW^2N$—, HO—$CW^2W^3$—NH—, $CH_2=CW^1$—CO—NH—, $CH_2=CH$—$(COO)_{k1}$-Phe-$(O)_{k2}$—, Phe-CH=CH—, HOOC—, OCN—, and $W^4W^5W^6Si$—, with $W^1$ being H, Cl, CN, phenyl or alkyl with 1 to 5 C-atoms, in particular H, $C_1$ or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2$=CH—COO—, $CH_2$=C($CH_3$)— COO—, $CH_2$=CH—, $CH_2$=CH—O—, $(CH_2$=CH$)_2$CH—OCO—, $(CH_2$=CH$)_2$CH—O—, and

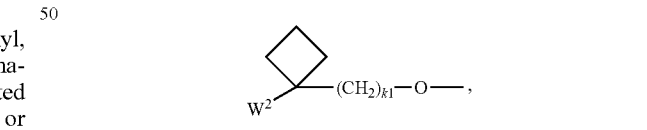

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As spacer group Sp all groups can be used that are known for this purpose to the skilled in the art. The spacer group Sp is preferably of formula Sp'-X, such that P-Sp- is P-Sp'-X— and P*-Sp- is P*-Sp'-X—, wherein Sp' is alkylene with up to 20 C atoms which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond, and R$^0$, R$^{00}$, X$^1$ and X$^2$ have one of the meanings given above. X is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— or a single bond, in particular —O—, —S—, —C≡C—, —CX$^1$=CX$^2$— or a single bond, very preferably a group that is able to from a conjugated system, such as —C≡C— or —CX$^1$=CX$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P-Sp- or P*-Sp- wherein Sp is a single bond.

In case of compounds with two groups P-Sp or P*-Sp-, respectively, each of the groups P or P* and the spacer groups Sp can be identical or different.

Another preferred embodiment relates to compounds comprising one or more groups P*-Sp-, wherein P* is a group that can be converted to or substituted by a polymerisable group P as defined above. Preferably P* is a group that is less reactive than P, for example towards spontaneous polymerisation. These compounds can be used for example as intermediates in the synthesis of polymerisable compounds of formula II having one or more groups P, or as a precursor material for polymerisable compounds which are too reactive to be stored or transported for longer periods of time. The group P* is preferably chosen such that it can easily be transformed into or substituted by a group P by known methods. For example, it can be a protected form of group P. Further preferred groups P* are for example —OH or silyl groups like —O—Si—R$^0$R$^{00}$R$^{000}$, for example —O—Si(CH$_3$)$_3$, —O—Si-(isopropyl)$_3$, —O—Si-(phenyl)$_3$, —O—Si—(CH$_3$)$_2$(phenyl), —O—Si(CH$_3$)$_2$(tert-butyl) or the like, which can be reacted e.g. into polymerisable (meth)acrylate end groups.

SCLCPs obtained from the inventive compounds or mixtures by polymerisation or copolymerisation have a backbone that is formed by the polymerisable group P.

The mono-, oligo- and polymers of the present invention can be synthesized according to or in analogy to known methods. Some preferred methods are described below.

Scheme 1:

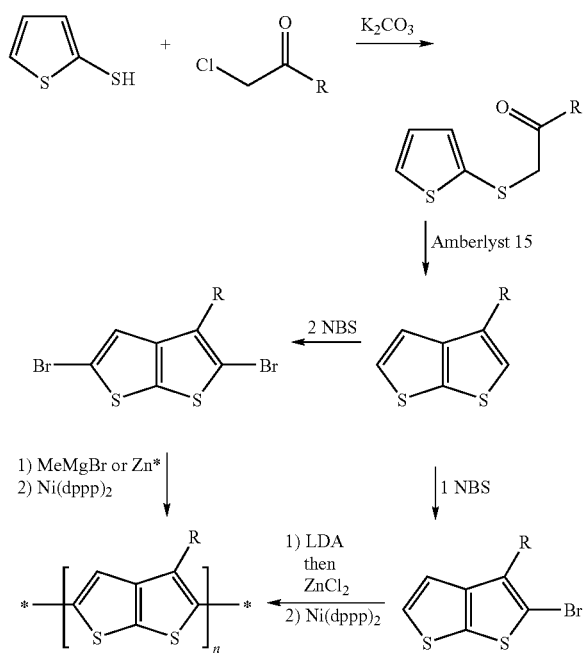

Thiophene-2-thiol is readily alkylated with 1-chloro-2-dodecanone (according to the procedure of C. Mahatsekake (Phosphorus, Sulfur and Silicon, 1990, 47, p 35). The resulting ketone is readily cyclised to the 2-alkyl-thieno[2,3-b]thiophene by treatment with an acid catalyst (amberlyst 15) in chlorobenzene. The resulting monomer is either mono- or dibrominated by treatment with either one or two equivalents of N-bromosuccinimide (NBS) in THF (scheme 1).

Polymerisation to the regioregular polymer is accomplished for example by one of the five following methods. According to the first method, firstly the 2-bromo-3-alkyl-thieno[2,3-b]thiophene is lithiated in the 5-position by treatment with a strong base such as LDA to form the lithium salt. This is converted to the organozinc reagent by treatment with anhydrous zinc chloride, and this intermediate is polymerised in situ by the addition of a bidentate nickel catalyst (in analogy to the method for thiophene derivatives as disclosed in R. D. McCullough et al., *J. Org. Chem.*, 1993, 58, 904).

According to the second method, the 2-5-dibromo-3-alkyl-thieno[2,3-b]thiophene is converted to the organozinc derivative directly by treatment with activated zinc, and this is polymerised by the addition of a bidentate nickel catalyst (in analogy to T.-A. Chen, R. D. Rieke, *J. Am. Chem. Soc.*, 1992, 114, 10087.).

According to the third method, the 2,5-dibromo-3-alkyl-thieno[2,3-b]thiophene is treated with one equivalent of a Grignard reagent to form the monogrignard reagent, which is again polymerised by the addition of a nickel catalyst (in analogy to S. M. K. Robert S. Loewe, and; R. D. McCullough*, *Adv. Mater.*, 1999, 11, 250).

According to the fourth method (scheme 2), the 2-bromo-3-alkyl-thieno[2,3-b]thiophene is lithiated in the 5-position by treatment with a strong base such as LDA to form the lithium salt. This is converted to an organotin reagent by treatment with a trialklytin chloride, which can be isolated and purified by chromatographic methods. Subsequent treatment of this intermediate with a transition metal catalyst, such as Pd(PPh$_3$)$_4$ affords the product (in analogy to A. Iragi, G. W. Barker, *J. Mater. Chem.*, 1998, 8, 25).

According to the five method (scheme 2), the 2-bromo-3-alkyl-thieno[2,3-b]thiophene is lithiated in the 5-position by treatment with a strong base such as LDA to form the lithium salt. This is converted to an organoboron reagent by treatment with an appropriate trialkoxyboron reagent, which can be isolated and purified by chromatographic methods. Subsequent treatment of this intermediate with a transition metal catalyst, such as Pd(PPh$_3$)$_4$ and a base, such as CsF or aqueous potassium carbonate affords the product (in analogy to S. Guillerez, G. Bidan, Synth. Metals, 1998, 93, 123).

Scheme 2:

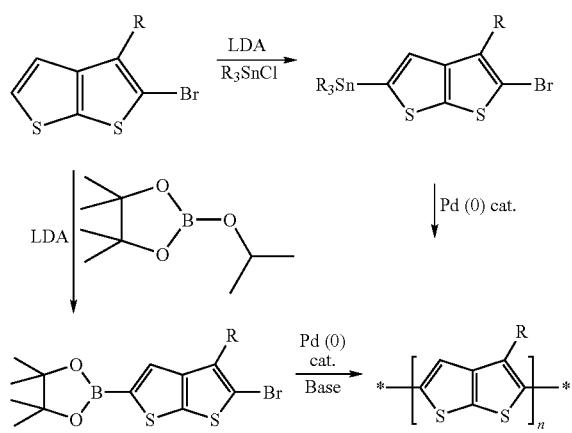

3,4-Dialkyl-thieno[2,3-b]thiophene can be conveniently synthesised in 3 steps from thieno[2,3-b]thiophene as shown in scheme 3. Thieno[2,3-b]thiophene is tetrabrominated by treatment with 4 equivalents of bromine in glacial acetic acid. Reduction with zinc in acetic acid removes the bromine substituents in the 2,5-positions. The resulting 3,4-dibromothieno[2,3-]thiophene is readily alkylated with a variety of zinc reagents by treatment with an organozinc halide in the presence of a transition metal catalyst. The resulting monomer can be polymerised chemically by treatment with iron (III) chloride to afford the homo polymer. Alternatively, bromination affords 2,5-dibromo-3,4-dialkylthieno[2,3-b]thiophene which can be used as a component in a co-polymerisation. Thus reaction with 2,5-bis(trimethylstannyl)thieno[2,3-b]thiophene in the presence of a palladium catalyst affords the co-polymer.

Scheme 3:

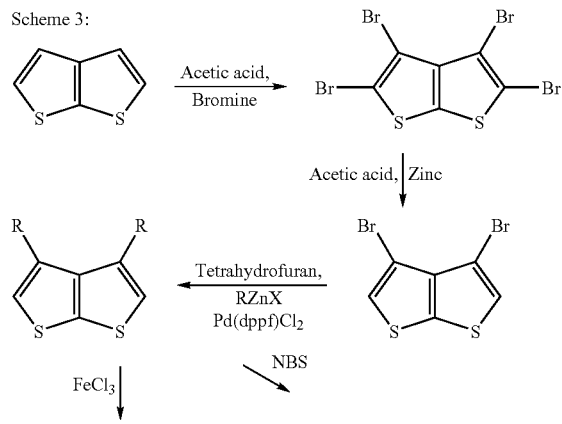

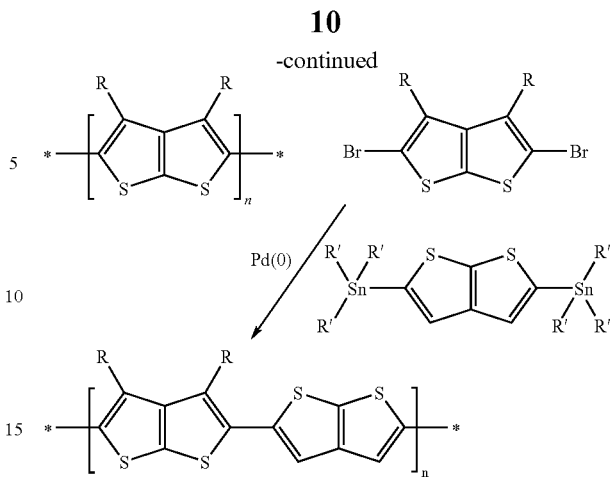

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, La$(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

A preferred embodiment of the present invention relates to mono-, oligo- and polymers of formula I and its preferred subformulae that are mesogenic or liquid crystalline, and very preferably comprise one or more polymerisable groups. Very preferred materials of this type are monomers and oligomers of formula I and its preferred subformulae wherein n is an integer from 1 to 15 and $R^3$ and/or $R^4$ denote P-Sp-.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

For example, if a device is made from a polymerisable liquid crystal material by polymerisation in situ, the liquid crystal material preferably comprises one or more mono- or oligomers of formula I and its preferred subformulae wherein one or both of $R^3$ and $R^4$ denote P-Sp-. If a liquid crystal polymer is prepared first, for example by polymerisation in solution, and the isolated polymer is used to make the device, the polymer is preferably made from a liquid crystal material comprising one or more mono- or oligomers of formula I and its preferred subformulae wherein one of $R^3$ and $R^4$ denotes P-Sp-.

It is also possible to copolymerise the polymerisable mono-, oligo- and polymers according to the present invention with other polymerisable mesogenic or liquid crystal monomers that are known from prior art, in order to induce or enhance liquid crystal phase behaviour.

Thus, another aspect of the invention relates to a polymerisable liquid crystal material comprising one or more mono-, oligo- or polymers of the present invention as described above and below comprising at least one polymerisable group, and optionally comprising one or more further polymerisable compounds, wherein at least one of the polymerisable mono-, oligo- and polymers of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the present invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Preferably polymerisation is carried out as in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P-Sp- can also be copolymerised with polymerisable mesogenic compounds to induce or enhance liquid crystal phase behaviour. Polymerisable mesogenic compounds that are suitable as comonomers are known in prior art and disclosed for example in WO 93/22397; EP 0,261,712; DE 195, 04,224; WO 95/22586 and WO 97/00600.

Another aspect of the invention relates to a liquid crystal side chain polymer (SCLCP) obtained from a polymerisable liquid crystal material as defined above by polymerisation or polymeranaloguous reaction. Particularly preferred are SCLCPs obtained from one or more monomers of formula I1 and its preferred subformulae wherein one or both, preferably one, of $R^3$ and $R^4$ are a polymerisable or reactive group, or from a polymerisable mixture comprising one or more of said monomers.

Another aspect of the invention relates to an SCLCP obtained from one or more monomers of formula I1 and its preferred subformulae wherein one or both of $R^3$ and $R^4$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397, EP 0 261 712, DE 195 04 224, WO 95/22586, WO 97/00600 and GB 2 351 734. Typical non mesogenic comonomers are for example alkyl acrylates or alkyl methacrylates with alkyl groups of 1 to 20 C atoms, like methyl acrylate or methyl methacrylate.

The mono-, oligo- and polymers of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

An OFET device according to the present invention preferably comprises:

a source electrode, a drain electrode, a gate electrode, a semiconducting layer, one or more gate insulator layers, optionally a substrate.

wherein the semiconductor layer comprises a compound of formula I.

The OFET device can be a top gate device or a bottom gate device. Suitable structures and manufacturing methods of an OFET device are known to the skilled in the art and are described in the literature, for example in WO 03/052841.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with monetry value, like stamps, tickets, shares, cheques etc.

Alternatively, the mono-, oligo- and polymers according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., Science, 279, 1998, 835-837.

According to another use, the inventive compounds, materials or films can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the polymers according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

The examples below serve to illustrate the invention without limiting it. In the foregoing and the following, all temperatures are given in degrees Celsius, and all percentages are by weight, unless stated otherwise.

Example 1

Poly(3-decylthieno[2,3-b]thiophene-2,5-diyl) (1) is prepared as follows.

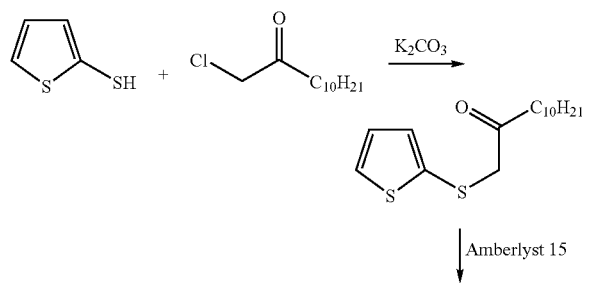

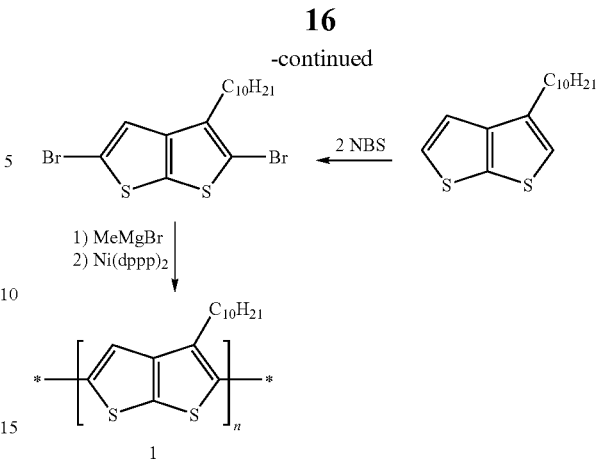

1-(Thiophen-2-ylsulfanyl)-dodecan-2-one

To a solution of thiophene-2-thiol (2.0 g, 17.2 mmol) in dry acetone (100 ml) is added anhydrous potassium carbonate (2.8 g; 20 mmol), followed by 1-chlorododecan-2-one (3.8 g, 17.2 mmol) dropwise. The reaction is stirred for 30 min and RT, filtered and concentrated under reduced pressure. The crude product is further purified by column chromatography (eluent: petrol/ethyl acetate 100:0 to 95:5) to afford the product as a colourless oil (3.66 g, 71%). M/Z 298 (M$^+$). $^1$H NMR (300 MHz, CDCl$_3$) δ 7.36 (1H, dd), 7.15 (1H, dd), 6.96 (1H, dd), 3.55 (2H, s), 2.55 (2H, t), 1.57 (2H, m), 1.35-1.20 (14H, m), 0.88 (3H, t). $^{13}$C NMR (75 MHz, CDCl$_3$) δ 205.1, 134.6, 132.5, 130.3, 127.7, 48.2, 41.1, 31.9, 29.6, 29.5, 29.4, 29.3, 29.1, 23.8, 22.7, 14.1.

3-Decyl-thieno[2,3-b]thiophene

A solution of 1-(thiophen-2-ylsulfanyl)-dodecan-2-one (3.40 g, 11.4 mmol) and amberlyst 15 (5.5 g) in chlorobenzene (200 mL) are refluxed over 4 A molecular sieves (Soxhlet) for 16 h. The reaction is cooled, filtered and concentrated under reduced pressure. The resulting residue is dissolved in petrol and filtered though a small plug of silica to remove coloured impurities. The organics are concentrated under reduced pressure and further purified by column chromatography over RP18 silica (eluant:acetonitrile). The first fraction is collected to afford the product as a colourless oil (1.8 g, 56%). M/Z 280 (M$^+$). $^1$H NMR (300 MHz, CDCl$_3$) δ 7.34 (1H, dd), 7.18 (1H, d), 6.93 (1H, d), 2.75 (2H, t), 1.70 (2H, quint), 1.40-1.20 (14H, m), 0.88 (3H, t). $^{13}$C NMR (75 MHz, CDCl$_3$) δ 147.3, 136.9, 135.1, 127.8, 122.4, 119.0, 31.9, 29.8, 29.65, 29.63, 29.50, 29.49 (2C), 29.4, 22.7, 14.2.

2,5-Dibromo-3-decylthieno[2,3-b]thiophene

To a solution of 3-decylthieno[2,3-b]thiophene (1.50 g, 5.35 mmol) in THF (20 ml) at 0° C. is added N-bromosuccinimde (1.98 g, 11.1 mmol) in 5 equal portions over 30 min. The reaction is stirred at RT for 72 h. A further portion of NBS (0.2 g, 1.1 mmol) is added and the reaction stirred an additional 1 h. The solvent is removed under reduced pressure, and the residue dissolved in ethyl acetate (50 ml) and washed with water (2×25 ml) and brine (2×25 ml), dried (Na$_2$SO$_4$), filtered and concentrated under reduced pressure. The residue is suspended in petrol and filtered through a silica plug, eluting with petrol. The organics are concentrated under reduced pressure to afford the product as a colourless oil (2.01 g, 86%). M/Z 436 (M+, 2%), 438 (M+, 4%), 440 (M+, 2%). $^1$H NMR (300 MHz, CDCl$_3$) δ 7.14 (1H, s), 2.69 (2H, t), 1.59 (2H, quint), 1.40-1.20 (14H, m), 0.88 (3H, t). $^{13}$C NMR (75 MHz, CDCl$_3$) δ 114.6, 134.5, 134.0, 122.2, 113.0, 110.0, 31.9, 26.93, 29.58, 29.44, 29.36 (2C), 29.0, 28.8, 22.7, 14.2. Elemental analysis for C$_{16}$H$_{22}$Br$_2$S$_2$: Calc. C, 43.85; H, 5.06. Found C, 43.5; H, 5.1.

Poly(3-decylthieno[2,3-b]thiophene-2,5-diyl)

To a solution of 2,5-dibromo-3-decylthieno[2,3-b]thiophene (0.88 g, 2 mmol) in dry THF (10 ml) at 0° C. is added a solution of diisopropyl magnesium bromide (1.02 ml of a 2.0M solution in diethyl ether, 2.04 mmol). The reaction is warmed to room temperature and stirred for 1 h at that temperature. An aliquot of the reaction mixture is quenched with water, and the organic extract analysed by GCMS to reveal 98% of the mono-Grignard product is formed in a 9:1 ratio of isomers. A portion of Ni(dppf)Cl$_2$ (28.0 mg, 2 mol %) is added at once as a solid and the reaction is heated in a microwave reactor (Emrys Creator, Personal Chemistry) at 160° C. for 20 min. The reaction is cooled, poured into methanol and stirred for 1 h. The resulting precipitate is filtered, washed with further methanol, acetone and hexane. The resulting brown powder is dissolved in chloroform and precipitated into a solution of methanol to afford and dried to afford a red powder (235 mg). GPC (chlorobenzene) Mn 7,500 g/mol; Mw 20,000 g/mol. $\lambda_{max}$ 320, 368, 382 (sh) nm (thin film). $^1$H NMR (300 MHz, CDCl$_3$) δ 7.28 (br s, 1H), 2.96 (br m, 1.6H), 2.85 (br m, 0.4H), 1.68 (br m, 2H), 1.45-1.1 (br m, 18H), 0.86 (br t, 3H) (NB The regioregularity is estimated to be between 80-85%. It is difficult to measure due to the low molecular weight of the polymer which causes interference from endgroups, and also because the proton adjacent to the backbone are poor resolved, probably due to aggregation effects).

Example 2

Poly(3,4-didodecyl-thieno[2,3-b]thiophene) (2) is prepared as follows.

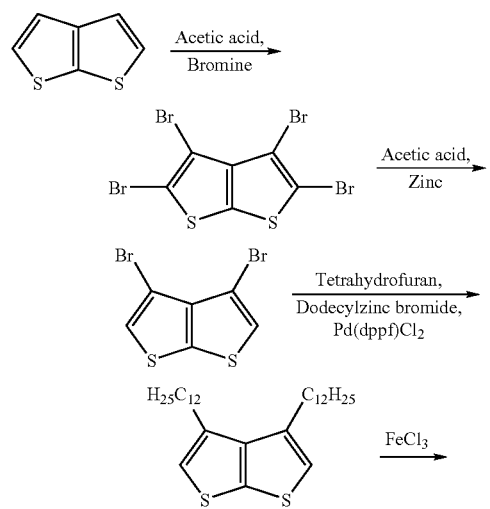

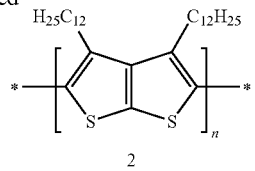

2,3,4,5-Tetrabromo-thieno[2,3-b]thiophene

To a solution of thieno[2,3-b]thiophene (0.74 g, 5.3 mmol) in acetic acid (60 ml) is added bromine (2 ml, 39 mmol). The reaction is refluxed for 1.5 h. After cooling, aqueous sodium sulfite solution (10% w/v) is added until the colour of the excess bromine has disappeared. The reaction mixture is extracted with dichloromethane, washed with saturated aqueous sodium carbonate solution, dried (Na$_2$SO$_4$), filtered and concentrated under reduced pressure. The product is purified by recrystallisation from hot methanol/dichloromethane to obtain fine pale yellow needles (1.59 g, 66%). M/Z (455, quintet, M+). Found C, 16.1; Br, 69.7. Calc. for C$_6$Br$_4$S$_2$C, 15.8; Br 70.1. NMR gave the expected signals.

3,4-Dibromo-thieno[2,3-b]thiophene

A mixture of 2,3,4,5-tetrabromothieno[2,3-b]thiophene (0.83 g, 1.8 mmol), zinc dust (0.29 g, 4.4 mmol), and acetic acid (30 ml) is refluxed for 2 h. The reaction mixture is poured into water, extracted with DCM, washed with aqueous saturated sodium carbonate solution, dried (Na$_2$SO$_4$), and concentrated under reduced pressure. The product is purified by recrystallisation from hot methanol to obtain white fibrous crystals (389 mg, 72%). M/Z (298, t, M+). Found C, 24.5; H, 0.8. Calc. for C$_6$H$_2$Br$_2$S$_2$C, 24.2; H, 0.7. $^1$H NMR (300 MHz, CDCl$_3$) δ 7.32 (s, 2H). $^{13}$C NMR (300 MHz, CDCl$_3$) δ 139.35, 137.42, 126.44, 102.96.

3,4-Didodecyl-thieno[2,3-b]thiophene

A microwave vial is charged with 3,4-dibromo-thieno[2,3-b]thiophene (1.02 g, 3.42 mmol), Pd(dppf)Cl$_2$ (57 mg, 0.09 mmol), sealed and purged with nitrogen. Anhydrous tetrahydrofuran (2 ml), then dodecylzinc bromide (16.8 ml of a 0.5M in THF, 8.4 mmol) is added and the reaction mixture is stirred at room temperature for 10 seconds, then heated in the microwave at 150° C. for 7 minutes. The reaction mixture is poured into dilute aqueous hydrochloric acid and extracted with dichloromethane. The organics are washed with water (until pH ~7), dried (Na$_2$SO$_4$), filtered and concentrated under reduced pressure. The product is purified by column chromatography on silica gel eluting with petrol (40-60° C.), then recrystallised in hot methanol/dichloromethane to obtain fine white needles (666 mg, 41%). M/Z 476 (M+). Found C, 75.5; H, 11.0; S, 14.2. Calc. for C$_{30}$H$_{52}$S$_2$C, 75.6; H, 11.0; S, 13.4. $^1$H NMR (300 MHz, CDCl$_3$) δ 6.90 (s, 2H), 2.82 (t, 4H, J=7.8 Hz), 1.69 (quint, 4H), 1.43 (m, 4H), 1.27 (m, 36H), 0.88 (t, 6H, J=6.6 Hz). $^{13}$C NMR (300 MHz, CDCl$_3$) δ 145.21, 137.85, 136.06, 122.30, 31.94, 30.36, 29.70, 29.67, 29.65, 29.58, 29.55, 29.44, 29.38, 22.70, 14.11

Poly(3,4-Didodecyl-thieno[2,3-b]thiophene) (2)

A solution of 3,4-didodecyl-thieno[2,3-b]thiophene (206 mg, 0.43 mmol) in chloroform (5 ml) is added dropwise to a stirred solution of ferric chloride (300 mg, 1.84 mmol) in chloroform (50 ml). The reaction is stirred for 48 h at room temperature with a constant flow of nitrogen bubbled into the reaction mixture to remove hydrochloric acid evolved. A concentrated solution of the dark blue residue in chloroform is precipitated into methanol (300 ml). The resulting precipitate is filtered and washed with methanol. The material is dedoped by stirring in concentrated aqueous ammonia solution (100 ml, 33%) for 1 h, filtered, washed with water then methanol to obtain a brown solid. The polymer is washed successively via Soxhlet extraction with methanol for 18 h, then acetone for 18 h. The polymer is dissolved in chloroform and precipitated into methanol to afford a brown solid, which is dried under vacuum (94 mg, 46%). GPC (chlorobenzene) Mn (9,600 g/mol), Mw (34,000 g/mol). $\lambda_{max}$ 320 nm (chloroform). $\lambda_{max}$ 330 nm (thin film). $^1$H NMR NMR (300 MHz, $C_6D_4Cl_2$, 50° C.) δ 2.7-2.4 (v. br s, 4H), 1.65-1.1 (br m, 40 h), 0.89 (br s, 6H).

Example 3

Poly(3,4-didodecyl-thieno[2,3-b]thiophene-2,5-diyl-co-thieno[2,3-b]thiophen-2,5-diyl-) (3) is prepared as follows.

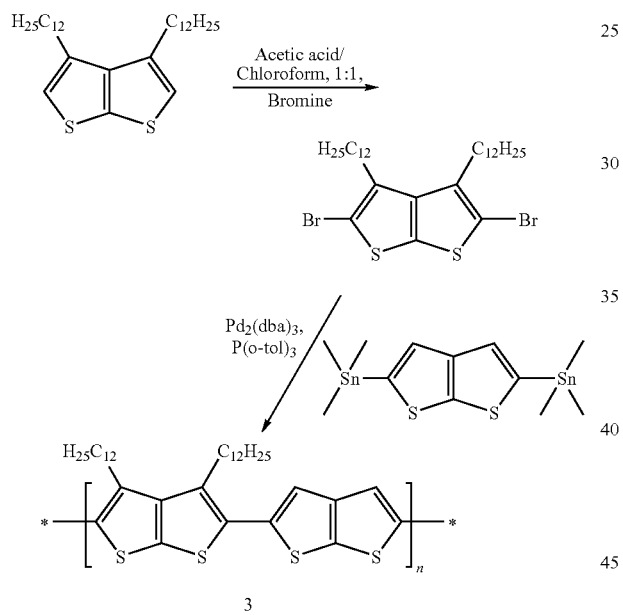

2,5-Dibromo-3,4-didodecylthieno[2,3-b]thiophene

To a solution of 3,4-didodecylthieno[2,3-b]thiophene (0.316 g, 0.75 mmol) in acetic acid (15 ml) and chloroform (15 ml) is added bromine (0.28 ml, 5.5 mmol) and the mixture is refluxed for 2 h. Aqueous sodium sulfite solution (10% w/v) is added until the colour of the excess bromine has disappeared. The reaction mixture is extracted with dichloromethane, washed with saturated aqueous sodium carbonate solution, dried ($Na_2SO_4$), filtered and concentrated under reduced pressure. The product is purified by column chromatography on silica gel, eluting with petrol (40-60° C.), then recrystallised in hot methanol/dichloromethane to obtain a white powder (325 mg, 75%). (Found C, 55.9; H, 8.0; Br, 25.2; S, 9.5. Calc. for $C_{30}H_{50}Br_2S_2C$, 56.8; H, 7.9; Br, 25.2; S, 10.1) $^1$H NMR (300 MHz, $CDCl_3$) δ 2.75 (t, 4H, J=7.93 Hz), 1.55 (quint, 4H), 1.42 (m, 4H), 1.27 (m, 32H), 0.88 (t, 6H, J=6.95 Hz).

Poly(2-thieno[2,3-b]thiophen-2-yl-co-3,4-didodecyl-thieno[2,3-b]thiophene) (3)

A dry microwave tube is charged with 2,5-dibromo-3,4-didodecylthieno[2,3-b]thiophene (150 mg, 0.236 mmol), 2,5-bis(trimethylstannyl)thieno[2,3-b]thiophene (110 mg, 0.236 mmol), tris(dibenzylideneacetone)dipalladium(0) (4.3 mg, 4.7 µmol), tri-o-tolylphosphine (5.7 mg, 19 µmol) and chlorobenzene (4.5 ml). The tube is sealed and degassed with nitrogen for 1 min, then heated in the microwave for 60 seconds at 140° C., followed by 60 seconds at 160° C., then 60 seconds at 180° C., and finally 600 seconds at 200° C. (fixed hold time). The reaction is cooled to 50° C. and then poured into methanol (90 ml)/concentrated hydrochloric acid (10 ml) and stirred overnight. The reaction is filtered though a soxhlet filter thimble and then extracted (soxhlet) with acetone (72 h), methanol (8 h) and petrol (40-60C; 14 h). The residue is dissolved in dichlorobenzene and precipitated into warm (50° C.) methanol to afford a brown powder (45 mg). GPC (chlorobenzene) Mn 9,400 g/mol, Mw 28,000 g/mol ($\lambda_{max}$ 327 nm (chloroform). $\lambda_{max}$ 326, 374, 398 (sh) nm (thin film). $^1$H NMR (300 MHz, $CDCl_3$, 50° C.) δ 7.28 (br s, 2H), 2.99 (br s, 4H), 1.68 (br s, 4H), 1.45-1.1 (br m, 36H), 0.87 (t, 6H).

The invention claimed is:

1. A polymer of formula I

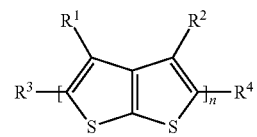

wherein $R^1$ and $R^2$ are independently of each other H, halogen, optionally substituted aryl or heteroaryl, P-Sp-, P*-Sp- or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —NR°—, —SiR°R°°—, —CO—, —COO—, —OCO—, —O—CO—O—, —S—CO—, —CO—S—, —CX$^1$═CX$^2$— or —C≡C— in such a manner that O and/or S atoms are not linked directly to one another, $R^3$ and $R^4$ independently of each other have one of the meanings of $R^1$ or denote —Sn(R°)$_3$, —B(OR')(OR"), —CH$_2$Cl, —CHO, —CH═CH$_2$ or —SiR°R°°R°°°, R°, R°°, R°°° are independently of each other H, aryl or alkyl with 1 to 12 C-atoms, R' and R" are independently of each other H or alkyl with 1 to 12 C-atoms, or OR' and OR" together with the boron atom form a cyclic group having 2 to 10 C atoms, $X^1$ and $X^2$ are independently of each other H, F, Cl or CN, P is a polymerizable group, P* is a group that can be converted to or substituted by a polymerizable group P, Sp is a spacer group or a single bond, n is an integer greater than 1, wherein the recurring units can be identical or different and, in at least one recurring unit one or both of $R^1$ or $R^2$ are not H.

2. The polymer according to claim 1, wherein only one of $R^1$ and $R^2$ is H.

3. The polymer according to claim 1, wherein $R^1$ and $R^2$ are different from H.

4. The polymer according to claim 1, wherein $R^1$ and $R^2$ are H, $C_1$-$C_{20}$-alkyl, $C_1$-$C_{20}$-alkoxy, $C_1$-$C_{20}$-alkenyl, $C_1$-$C_{20}$-alkynyl, $C_1$-$C_{20}$-thioalkyl, $C_1$-$C_{20}$-silyl, $C_1$-$C_{20}$-ester, $C_1$-$C_{20}$-amino or $C_1$-$C_{20}$-fluoroalkyl.

5. The polymer according to claim 1, wherein n is an integer from 2 to 5000.

6. The polymer according to claim 1, having a regioregularity of head-to-tail couplings of 95% or more.

7. The polymer according to claim 1, of the following formulae

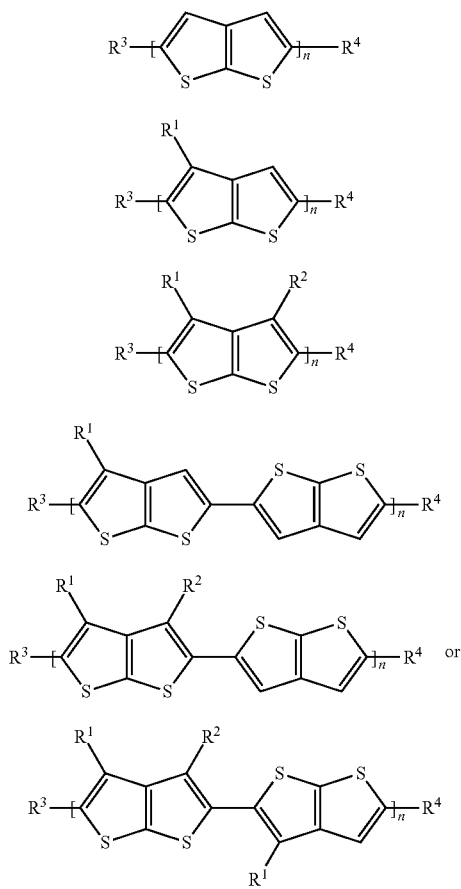

wherein $R^{1-4}$ have independently of each other one of the meanings of formula I different from H, n is as defined in formula I, and m is n/2.

8. Polymerisable liquid crystal material comprising one or more thienothiophene polymers according to claim 1 and one or more further polymerizable compounds, wherein at least one of said thienothiophene polymer or said further polymerizable compounds is mesogenic or liquid crystalline.

9. An anisotropic polymer film with charge transport properties obtainable from a polymer according to claim 1 that is aligned in its liquid crystal phase into macroscopically uniform orientation and polymerized or crosslinked to fix the oriented state.

10. The polymer according to claim 1, which is a side chain liquid crystal polymer obtained by polymerization of one or more corresponding monomers or by grafting said corresponding monomer to a polymer backbone in a polymeranaloguous reaction, optionally with one or more additional mesogenic or non-mesogenic comonomers.

11. In semiconductors, charge transport materials in optical, electrooptical or electronic devices, field effect transistors (FET) as components of integrated circuitry, thin film transistors (TFT) in flat panel display applications, liquid crystal displays (LCD), Radio Frequency Identification (RFID) tags, or in semiconducting components for displays or organic light emitting diodes (OLED) comprising a polymerizable liquid crystalline polymer, the improvement comprising of the polymer of claim 1.

12. In electroluminescent materials, OLEDs, electroluminescent displays, backlights of displays, in photovoltaic or sensor devices, electrode materials in batteries, photoconductors, electrophotographic applications, organic memory devices, processes of detecting and discriminating DNA sequences, or alignment layers in LCD or OLED devices comprising a polymerizable liquid crystalline polymer, the improvement comprising of the polymer of claim 1.

13. A semiconducting, electroluminescent or charge transport material, component or device comprising at least one polymer according to claim 1.

14. An optical, electrooptical or electronic device, FET, integrated circuit (IC), TFT, OLED or alignment layer comprising a polymer according to claim 1.

15. A TFT or TFT array in flat panel displays, radio frequency identification (RFID) tag, electroluminescent display or backlight, comprising a device, FET, IC, TFT or OLED according to claim 14.

16. Security marking or device comprising a FET or an RFID tag according to claim 15.

17. A polymer according to claim 1, which is oxidatively or reductively doped to form conducting ionic species.

18. A charge injection layer, planarising layer, antistatic film or conducting substrate or pattern for electronic applications or flat panel displays, comprising a polymer according to claim 1.

* * * * *

UNITED STATES PATENT AND TRADEMARK OFFICE
CERTIFICATE OF CORRECTION

PATENT NO. : 8,114,316 B2
APPLICATION NO. : 11/573983
DATED : February 14, 2012
INVENTOR(S) : Heeney et al.

It is certified that error appears in the above-identified patent and that said Letters Patent is hereby corrected as shown below:

Column 21, line 12 delete formula "Ia"

Signed and Sealed this
Twentieth Day of November, 2012

David J. Kappos
*Director of the United States Patent and Trademark Office*